(12) United States Patent
Bagley

(10) Patent No.: US 11,266,407 B2
(45) Date of Patent: Mar. 8, 2022

(54) WIDE ROTATING CLIP

(71) Applicant: Boston Scientific Scimed, Inc., Maple Grove, MN (US)

(72) Inventor: Kevin L. Bagley, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 54 days.

(21) Appl. No.: 16/822,676

(22) Filed: Mar. 18, 2020

(65) Prior Publication Data
US 2020/0345368 A1 Nov. 5, 2020

Related U.S. Application Data

(60) Provisional application No. 62/840,820, filed on Apr. 30, 2019.

(51) Int. Cl.
*A61B 17/08* (2006.01)
*A61B 17/122* (2006.01)
*A61B 17/128* (2006.01)

(52) U.S. Cl.
CPC .......... *A61B 17/083* (2013.01); *A61B 17/122* (2013.01); *A61B 17/1227* (2013.01); *A61B 17/1285* (2013.01)

(58) Field of Classification Search
CPC ............ A61B 17/083; A61B 17/32002; A61B 2017/00473; A61B 17/1285; A61B 17/1227; A61B 17/12; A61B 17/85; A61B 17/1277; A61B 17/122; A61B 17/128; A61B 17/10; A61B 17/08; A61B 17/29; A61B 2017/081; A61B 2017/088; A61B 2017/2926; A61B 2017/2927; A61B 2017/2929; A61B 2017/293; A61B 2017/2931; A61B 2017/2947; A61F 5/0086

See application file for complete search history.

(56) References Cited

U.S. PATENT DOCUMENTS 5,649,938 A * 7/1997 Allen .................. A61B 17/1114
606/144
5,649,957 A * 7/1997 Levin ..................... A61B 17/29
606/205

(Continued)

FOREIGN PATENT DOCUMENTS

WO 2017/191583 11/2017

*Primary Examiner* — Dianne Dornbusch
(74) *Attorney, Agent, or Firm* — Fay Kaplun & Marcin, LLP

(57) ABSTRACT

A clipping device includes a capsule and a pair of clip arms, proximal ends of the clip arms slidably received within the channel of the capsule such that the clip arms are movable relative to the capsule between an open configuration and a closed configuration. The clipping device also includes a pair of jaws, each of the jaws pivotally coupled to a corresponding one of the clip arms and movable relative to the clip arms between an insertion configuration, in which longitudinal axes of the pair of jaws are substantially aligned with longitudinal axes of the clip arms, and a tissue-receiving configuration, in which the longitudinal axes of the pair of jaws extend transverse to the longitudinal axes of the clip arms, the pair of jaws movable toward the tissue-receiving configuration when the pair of clip arms are in the open configuration.

20 Claims, 5 Drawing Sheets

(56) References Cited

U.S. PATENT DOCUMENTS

| | | | |
|---|---|---|---|
| 5,766,189 A * | 6/1998 | Matsuno | A61B 17/122 606/139 |
| 5,984,939 A * | 11/1999 | Yoon | A61B 17/12013 606/139 |
| 9,445,821 B2 | 9/2016 | Wells et al. | |
| 2011/0054498 A1 | 3/2011 | Monassevitch et al. | |
| 2013/0226200 A1 * | 8/2013 | Kappel | A61B 17/1285 606/142 |
| 2014/0031860 A1 * | 1/2014 | Stoddard | A61B 17/29 606/205 |
| 2019/0105046 A1 | 4/2019 | Jagelski et al. | |

* cited by examiner

WIDE ROTATING CLIP

PRIORITY CLAIM

The present disclosure claims priority to U.S. Provisional Patent Application Ser. No. 62/840,820 filed Apr. 30, 2019; the disclosure of which is incorporated herewith by reference.

FIELD

The present disclosure relates to endoscopic devices and, in particular, relates to endoscopic clipping devices for treating tissue along the gastrointestinal tract.

BACKGROUND

Physicians have become more willing to perform aggressive interventional and therapeutic endoscopic gastrointestinal (GI) procedures, which may increase the risk of perforating the wall of the GI tract, or may require closure of the GI tract wall as part of the procedure. Currently, smaller defects may be treated using a through-the-scope clip. Mid-range defects, however, may require multiple through-the-scope clips or over-the scope clips, which may be difficult to position as desired. Even larger defects may require treatment via suturing, which is often cumbersome.

SUMMARY

The present disclosure relates to a clipping device comprising a capsule extending longitudinally from a proximal end to a distal end, and including a channel extending therethrough. A pair of clip arms may extend from proximal ends to distal ends, the proximal ends being slidably received within the channel of the capsule such that the pair of clip arms are movable relative to the capsule between an open configuration, in which the distal ends are separated from one another, and a closed configuration, in which the distal ends are moved toward one another. The clipping device also comprises a pair of jaws, each of the jaws pivotally coupled to a corresponding one of the clip arms, and movable relative to the clip arms between an insertion configuration, in which longitudinal axes of the pair of jaws are substantially aligned with longitudinal axes of the clip arms, and a tissue-receiving configuration, in which the longitudinal axes of the pair of jaws extend transverse to the longitudinal axes of the clip arms so that a target tissue is receivable between the pair of jaws along a length thereof. The pair of jaws may be movable toward the tissue-receiving configuration when the pair of clip arms are in the open configuration.

In an embodiment, each of the pair of jaws may be coupled to the distal end of the corresponding one of the clip arms via a pin extending through a midpoint of each of the pair of jaws and the distal end of the corresponding one of the clip arms.

In an embodiment, the pair of clip arms may be biased toward the open configuration so that the pair of clip arms are constrained toward the closed configuration via an interior surface of the capsule.

In an embodiment, longitudinal edges of each of the pair of clip arms may include retaining structures extending toward a central plane extending between the pair of clip arms. The retaining structures may maintain a position of a corresponding one of the jaws relative to the clip arms in the insertion configuration.

In an embodiment, the retaining structures may be configured to permit pivoting of the pair of jaws relative to the pair of clip arms up to an angle of approximately 10 degrees.

In an embodiment, each of the pair of jaws may extend longitudinally from a first end to a second end and include a bend therealong so that the first and second ends extend toward the central plane.

In an embodiment, each of the pair of jaws may be biased toward the tissue-receiving configuration via a torsion spring so that the pair of jaws are restrained toward the insertion configuration via the retaining structures when the clip arms are in the closed configuration.

In an embodiment, each of the pair of jaws may be elastically deformable toward a straightened configuration, when the pair of clip arms is in the closed configuration.

In an embodiment, at least one of the pair of jaws may include gripping features extending along a longitudinal edge thereof.

The present disclosure also relates to a device for treating a target tissue, comprising a clip including a capsule extending longitudinally from a proximal end to a distal end and including a channel extending therethrough. Proximal ends of a pair of clip arms may be slidably received within the channel so that the pair of clip arms are movable relative to the capsule between an open configuration, in which distal ends thereof are separated from one another, and a closed configuration, in which the distal ends thereof are moved toward one another. A pair of jaws may be pivotally coupled to the clip arms and movable relative to the clip arms between an insertion configuration, in which longitudinal axes of the pair of jaws are substantially aligned with longitudinal axes of the clip arms, and a tissue-receiving configuration, in which the longitudinal axes of the pair of jaws extend transverse to the longitudinal axes of the clip arms. A proximal portion of the device is configured to permit insertion of the clip through a working channel of an endoscope, the proximal portion including a bushing at a distal end thereof, the bushing releasably coupled to the proximal end of the capsule.

In an embodiment, the pair of clip arms may be biased toward the open configuration so that the pair of clip arms are constrained toward the closed configuration via an interior surface of the capsule.

In an embodiment, longitudinal edges of each of the pair of clip arms may include retaining structures extending toward a central plane extending between the pair of clip arms. The retaining structures may maintain a position of a corresponding one of the jaws relative to the clip arms in the insertion configuration.

In an embodiment, each of the pair of jaws may extend longitudinally from a first end to a second end and include a bend therealong so that the first and second ends extend toward the central plane.

In an embodiment, each of the pair of jaws may be biased toward the tissue-receiving configuration via a torsion spring so that the pair of jaws are restrained toward the insertion configuration via the retaining structures when the clip arms are in the closed configuration.

In an embodiment, at least one of the pair of jaws may include gripping features extending along a longitudinal edge thereof.

The present disclosure also relates to a method for treating a target tissue comprising inserting a clip device, in a closed configuration, through a working channel of an endoscope to a target site within a body until the clip device extends distally past a distal end of the working channel. The clip device may include a capsule and a pair of clip arms received therein and movable relative thereto between an open configuration, in which distal ends of the clip arms are separated from one another, and the closed configuration, in which the distal ends of the clip arms are drawn toward one another. The clip device may move toward the open configuration so that a pair of jaws pivotally coupled to distal ends of the clip arms are moved from an insertion configuration, in which longitudinal axes of the pair of jaws are aligned with longitudinal axes of the clip arms, toward a tissue-receiving configuration in which the pair of jaws extend transverse relative to the clip arms. Each of the pair of jaws may be pivotally coupled to a corresponding one of the clip arms. The pair of jaws may be positioned over the target tissue so that the target tissue is received therebetween. The pair of arms may be moved, with the jaws extending transverse relative thereto, toward the closed configuration to grip the target tissue between the pair of jaws.

DETAILED DESCRIPTION

Figure 1:
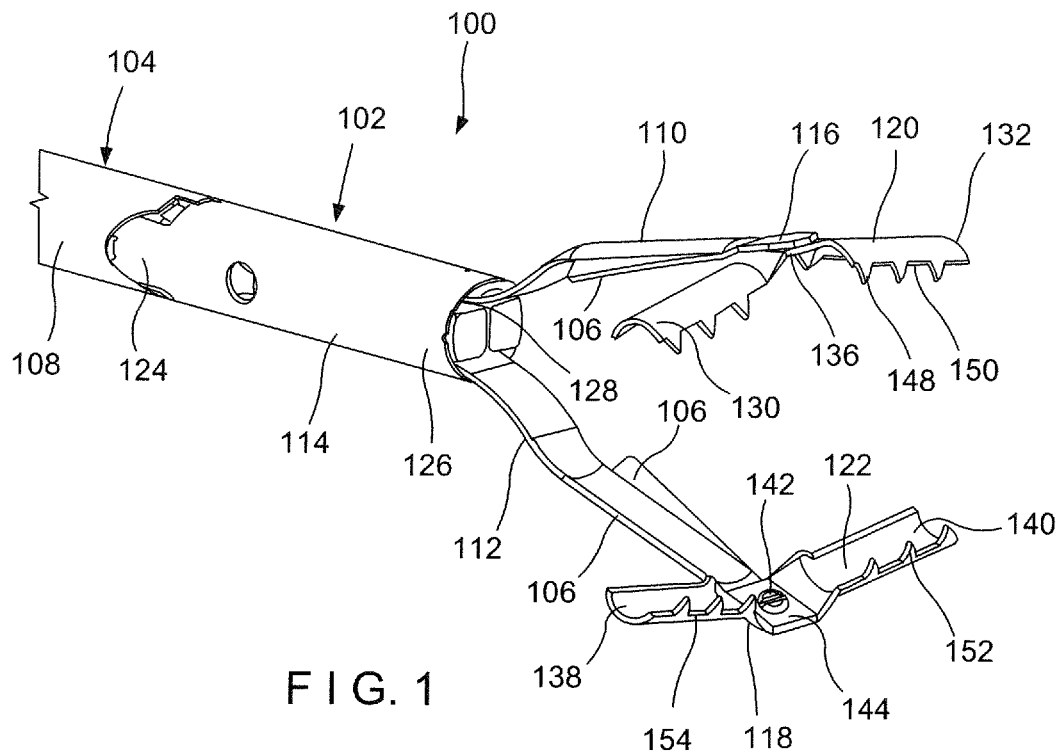
FIG. 1 shows a perspective view of a device according to an exemplary embodiment of the present disclosure, in an open, tissue-receiving configuration.

The present disclosure may be further understood with reference to the following description and the appended drawings, wherein like elements are referred to with the same reference numerals. The present disclosure is directed to an endoscopic clipping device for treating tissue perforations, defects and/or bleeds. Exemplary embodiments of the present disclosure describe a clip comprising clip arms and jaws rotatable relative to the arms so that, upon opening of the clip arms, the jaws rotate toward a T-shaped configuration suitable for closing and/or treating larger tissue than can be dealt with by traditional through-the scope clips, i.e., tissue openings that would previously have likely required multiple clips to close. It should be noted that the terms proximal and distal, as used herein, are intended to refer to a direction toward (proximal) and away from (distal) a user of the device.

As shown in FIGS. 1-12, a device 100 for treating a tissue defect comprises a clip 102 releasably connected to a proximal portion 104 including, for example, a handle member (not shown) connected to the clip 102 via a flexible shaft extending distally from the handle member to a bushing 108 releasably coupled to the clip 102 so that the clip 102 may be inserted to a target site within a body via a working channel of an endoscope inserted, for example, through a body lumen accessed via a natural bodily orifice. The clip 102 includes a first clip arm 110 and a second clip arm 112, proximal ends of which are received within a capsule 114 and movable relative thereto between an open configuration, in which distal ends 116, 118 of the first and second clip arms 110, 112, respectively, are separated from one another, and a closed configuration, in which the distal ends 116, 118 are drawn toward one another.

The clip 102 also includes a first jaw 120 rotatably coupled to a distal end 116 of the first arm 110 and a second jaw 122 rotatably coupled to a distal end 118 of the second arm 112 such that the first and second jaws 120, 122 are rotatable relative to the first and second clip arms 110, 112 between an insertion configuration and a tissue-receiving configuration. In the insertion configuration, the first and second clip arms 110, 112 are in the closed configuration and the first and second jaws 120, 122 are substantially aligned therewith with a length of each of the first and second jaws 120, 122 extending substantially parallel to a longitudinal axis L of the capsule 114. In the tissue-receiving configuration, the clip 102 is moved to the open configuration and the first jaw 120 and the second jaw 122 are rotated relative to the first and second clip arms 110, 112, respectively, to extend transverse relative thereto (i.e., transverse to the axis L).

A length of the first and second jaws 120, 122 is preferably selected to facilitate the treatment of larger tissue defects which would have previously required multiple clips to close. For example, the first and second jaws may be from 3 mm to 12 mm in length. It will be understood by those of skill in the art, however, that the first and second jaws 120, 122 may have any of a variety of lengths to suit a variety of tissue defect sizes. In one embodiment, the first and second jaws 120, 122 extend substantially symmetrically from a respective clip arm 110, 122.

As described above, the first and second clip arms 110, 112 are received within and movable relative to the capsule 114. In particular, the capsule 114 extends longitudinally along the axis L from a proximal end 124 releasably coupled to the bushing 108 to a distal end 126. A channel 128 extends longitudinally therethrough. The first and second clip arms 110, 112 extend from proximal ends slidably housed within the channel 128 to distal ends 116, 118. Proximal ends of the first and second clip arms 110, 112 are releasably connected to a control wire, which extends through the capsule 114 to the handle member of the device 100 to control longitudinal movement of the first and second clip arms 110, 112 relative to the capsule 114.

In one embodiment, the first and second clip arms 110, 112 are biased toward the open configuration. In the closed configuration, when the first and second clip arms 110, 112 are received within the capsule 114, the first and second clip arms 110, 112 are constrained in close proximity via an interior surface of the capsule 114. As the first and second clip arms 110, 112 are moved distally out of the capsule 114, the natural bias of the arms springs the arms 110, 112 away from one another toward the open configuration. Those skilled in the art will understand that a shape of at least a portion of each of the first and second clip arms 110, 112 may correspond to a shape of the capsule 114. For example, the capsule 114 according to this embodiment is substantially cylindrical and a portion of each of the first and second clip arms 110, 112 is curved to correspond to the cylindrical shape of the capsule 114.

Figure 11:
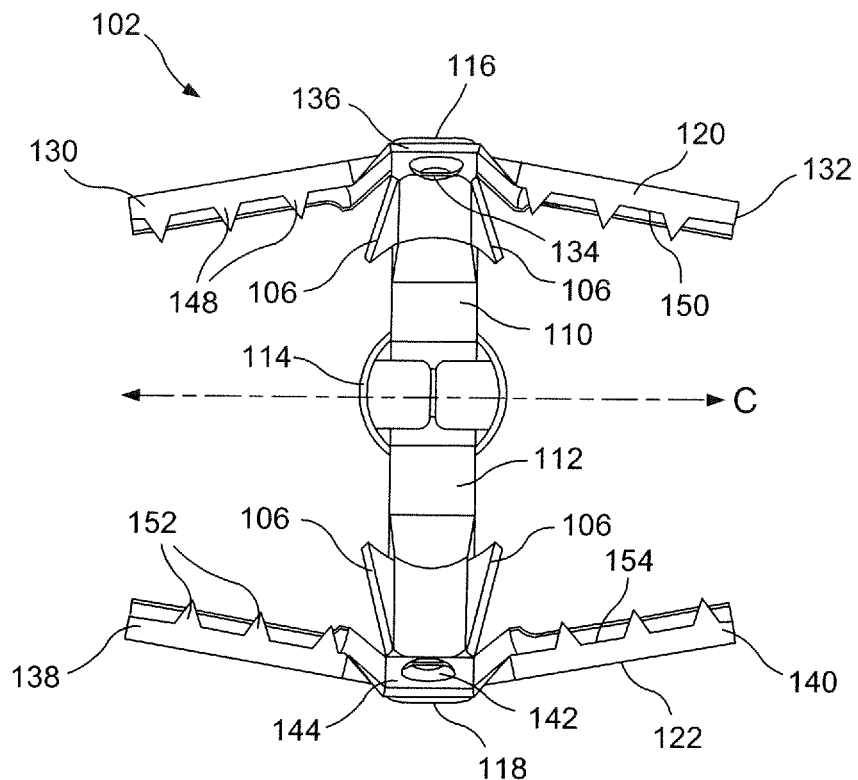
FIG. 11 shows a plan view from a distal end of the device of FIG. 1, in the open, tissue-receiving configuration.

In one embodiment, a portion of each of the first and second clip arms 110, 112 is curved about the longitudinal axis L of the capsule 114 to define retaining structures 106 which extend toward a central plane C extending between the first and second clip arms 110, 112, as shown in FIG. 11. As will be described in further detail below, these retaining structures 106 mate with correspondingly shaped portions of the jaws 120, 122 to aid in holding the first and second jaws 120, 122 in the insertion configuration, when the first and second clip arms 110, 112 are in the closed configuration. Although the retaining structures 106 are shown and described as defined via curved portions of the clip arms 110, 112, it will be understood by those of skill in the art that the retaining structures 106 may include any of a variety of structures extending from longitudinal edges of the first and second clip arms 110, 112, toward the central plane C, to retain the jaws 120, 122 therebetween, when the clip 102 is in the closed, insertion configuration.

Although not shown, the first and second clip arms 110, 112 of this embodiment additionally include a locking feature such as, for example, a locking tab extending laterally outward from a proximal portion thereof so that when the locking tab is received a corresponding locking structure of the capsule 114, the clip 102 is locked in the closed configuration. The corresponding locking structure of the capsule 114 may include, for example, an opening or window extending through a wall of the capsule 114 or a shoulder or detent formed by a portion of an inner surface of the capsule 114.

The first jaw 120 extends along a longitudinal axis from a first end 130 to a second end 132. The first jaw 120 is rotatably coupled to an interior surface of the first clip 110 at the distal end 116 thereof. In one example, the first jaw 120 is coupled to the first arm 110 via a pin 134 coupling the distal end 116 to a midpoint 136 of the first jaw 120 so that the first jaw 120 is rotatable about the pin 134 between the insertion configuration, in which the longitudinal axis of the first jaw 120 is substantially aligned with a longitudinal axis of the first arm 110, and a tissue-receiving configuration, in which the longitudinal axis of the first jaw 120 extends transverse relative to the longitudinal axis of the first arm 110. For example, the first jaw 120 may extend substantially perpendicular relative to the first arm 110 to form a T-shaped configuration therewith, when in the tissue-receiving configuration.

The first jaw 120 may also include gripping features such as, for example, teeth 148 extending along at least one longitudinal edge 150 thereof. In one example, the teeth 148 extend along the longitudinal edge 150 which, when the first jaw 120 is in the tissue-receiving configuration, extends distally of the other longitudinal edge. In addition, the first jaw 120 may include a slight bend along a portion thereof. In one example, as shown in FIG. 11, the first jaw 120 is bent at the midpoint 136 such that, when the clip 102 is in the open, tissue-receiving configuration, the first and second ends 130, 132 extend toward the central plane. In other words, a first portion of a length of the first jaw 120 is angled with respect to a second portion of a length of the first jaw 120. An angle between the first portion and the second portion of the length of the first jaw 120 may range from between 0 and 45 degrees. In one particular embodiment, the first portion and the second portion of the length of the first jaw 120 may be angled at approximately 20 degrees relative to one another.

Similarly to the first jaw 120, the second jaw 122 extends along a longitudinal axis from a first end 138 to a second end 140 and is rotatably coupled to an interior surface of the second clip 112 at the distal end 118 thereof. In one example, a midpoint 144 of second jaw 122 is coupled to the second arm 112 via a pin 142 about which the second jaw 122 may rotate relative to the second arm 112 between the insertion configuration, in which the longitudinal axis of the second jaw 122 is substantially aligned with a longitudinal axis of the second arm 112, and the tissue-receiving configuration, in which the longitudinal axis of the second jaw 122 extends transverse (e.g., perpendicular) relative to the longitudinal axis of the second arm 112.

Similarly to the first jaw 120, the second jaw 122 may also include gripping features such as, for example, teeth 152 along at least one longitudinal edge 154 of the second jaw 122. In one embodiment, the teeth 152 extend along the longitudinal edge 154 which extends distally of the other longitudinal ledge, when the clip 102 is in the tissue-receiving configuration. Thus, when the first and second clip arms 110, 112 are moved toward the closed configuration to grip the tissue received between the first and second jaws 120, 122, the tissue is gripped via the teeth 148, 152 along the distal longitudinal edges 150, 154. The second jaw 122 may also be bent at the midpoint 144 so that the first and second ends 138, 140 thereof extend toward the central plane C, as shown in FIG. 11. In other words, a first portion of a length of the second jaw 122 is angled with respect to a second portion of a length of the second jaw 122.

In one embodiment, an angle between the first and second portions of the length of the second jaw 122 may range from between 0 and 45 degrees, and in one particular embodiment, may be approximately 20 degrees. Although the first and second jaws 120, 122 are described and shown as including a bend at the midpoints 136, 144, it will be understood by those of skill in the art that the first and second jaws 120, 122 may include bends having any of a variety of configurations so long as the first and second ends 130, 132 and 138, 140, respectively, extend toward the central plane C. In another embodiment, for example, the first and second jaws 120, 122 may have substantially arched shapes. In another example, the first and second jaws 120, 122 may include bends along portions thereof other than the midpoints 136, 144.

Figure 2:
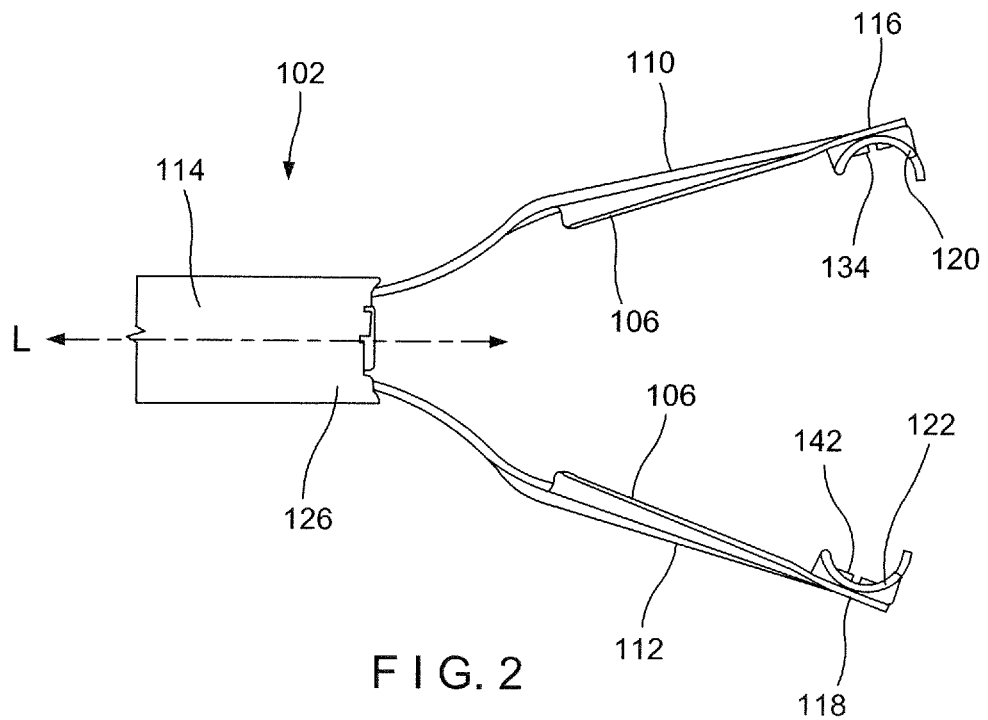
FIG. 2 shows a longitudinal side view of the device of FIG. 1, in the open, tissue-receiving configuration.
Figure 3:
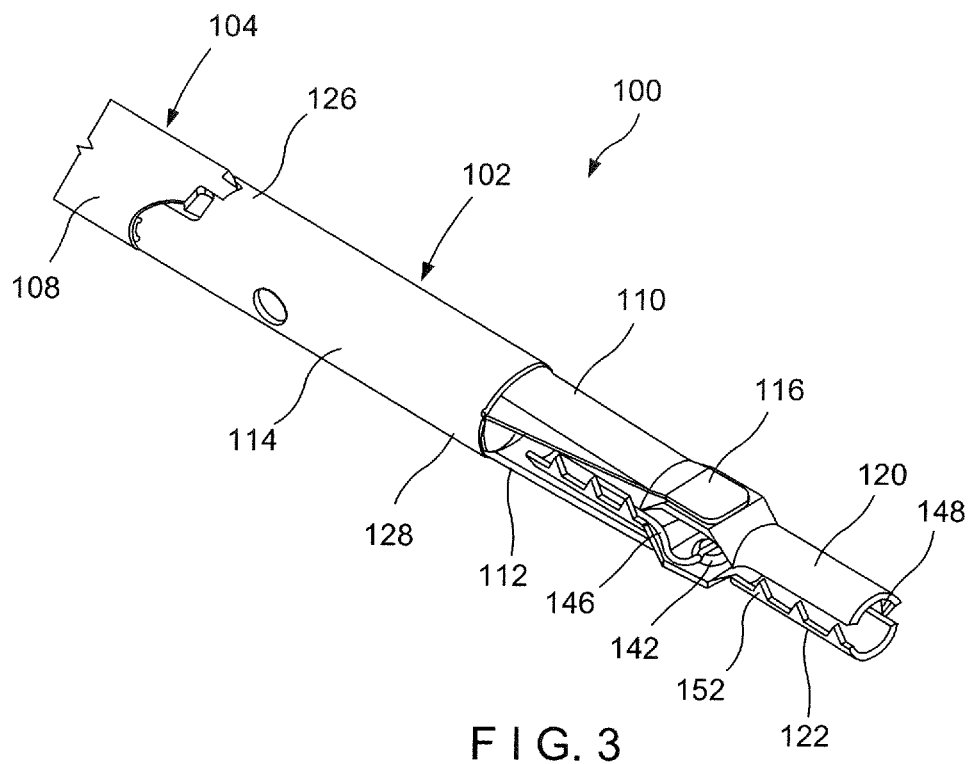
FIG. 3 shows a perspective view of the device of FIG. 1, in a closed, insertion configuration.
Figure 4:
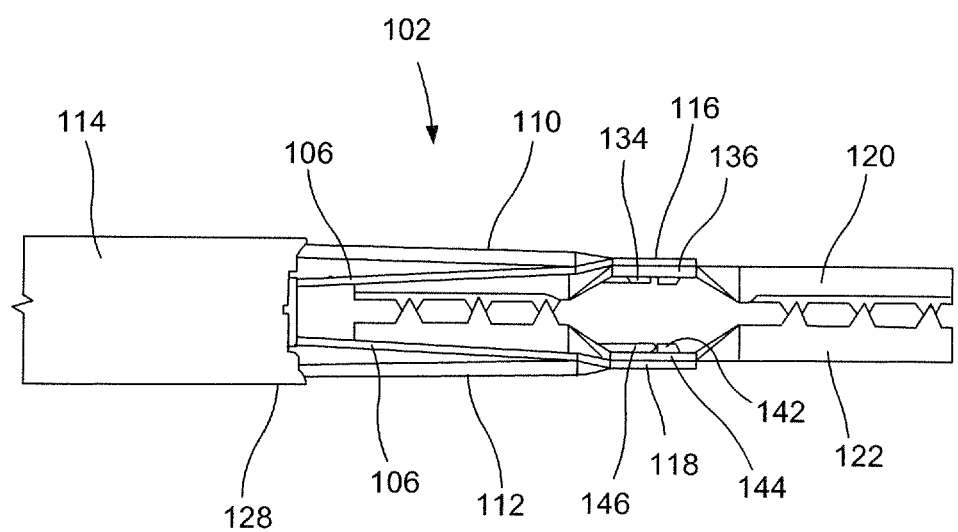
FIG. 4 shows a longitudinal side view of the device of FIG. 1, in the closed, insertion configuration.

Each of the first and second jaws 120, 122 in this embodiment is biased toward the tissue-receiving configuration via a biasing member such as a torsion spring 146. In the tissue-receiving configuration, as shown in FIGS. 1-2, longitudinal axes of the first and second jaws 120, 122 extend substantially parallel to one another and transverse to the axis L and the clip arms 110, 112 so that a portion of tissue wider than a width of the clip arms 110, 112 may be received and gripped therebetween. The first and second jaws 120, 122 are, in this embodiment, constrained toward the insertion configuration, as shown in FIGS. 3-4, via the interaction of the retaining structures 106 of the first and second clip arms 110, 112, when the first and second clip arms 110, 112 are in the closed configuration within the capsule 114. In particular, according to one embodiment, as described above, retaining structures 106 may be defined via portions of the first and second clip arms 110, 112 that are curved about the longitudinal axis L toward the central plane C to mate with correspondingly shaped portions of the jaws 120, 122 and aid in holding the first and second jaws 120, 122 in the insertion configuration, when the first and second clip arms 110, 112 are in the closed configuration. Those skilled in the art, however, will understand that other types of retaining structures 106 may be utilized without departing from the scope of the present embodiments.

In particular, as described above, at least a portion of each of the first and second clip arms 110, 112 is curved about the longitudinal axis of the clip 102 in a manner corresponding to a curvature of a corresponding part of the respective jaw 120, 122 to define retaining structures 106. When the first and second clip arms 110, 112 are in the closed configuration, the first and second jaws 120, 122 are pressed against one another, causing the first and second jaws 120, 122 to be elastically deformed toward a straight configuration. In other words, an angle at which the first and second jaws 120, 122 are bent at the midpoints 136, 144 is increased so that the first and second jaws 120, 122 are held in alignment with the first and second clip arms 110, 112, between the retaining structures 106 thereof. Thus, when the clip is in the closed, insertion configuration, the first and second jaws 120, 122 are prevented from rotating toward the tissue receiving configuration toward which they are biased.

Figure 5:
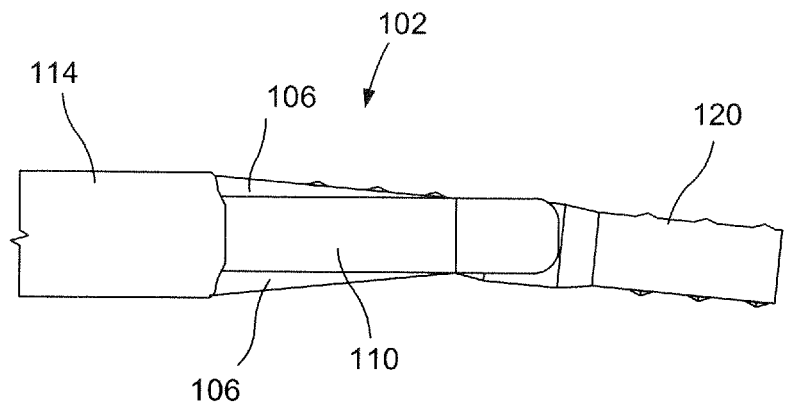
FIG. 5 shows a top plan view of the device of FIG. 1, illustrating an extent to which a jaw of a clip of the device is movable relative to an arm of the clip, in a first direction.
Figure 6:
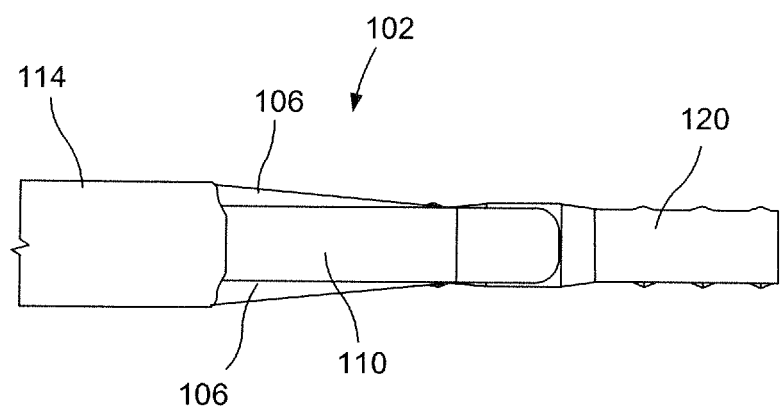
FIG. 6 shows a top plan view of the device of FIG. 1, in which a longitudinal axis of the jaw of the clip is substantially aligned with a longitudinal axis of the clip arm.
Figure 7:
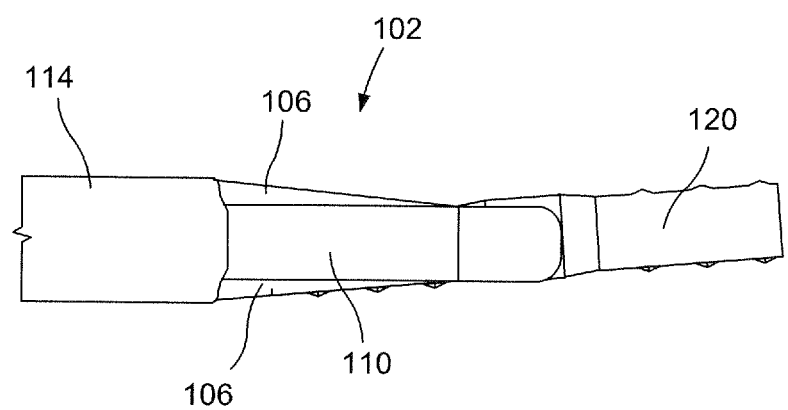
FIG. 7 shows a top plan view of the device of FIG. 1, illustrating the extent to which the jaw of the clip is movable relative to the arm of the clip, in a second direction.

In one embodiment, as shown in FIGS. 5-7, the retaining structures 106 of each of the first and second clip arms 110, 112 and the first and second jaws 120, 122 are correspondingly sized and shaped to permit slight movements of the first and second jaws 120, 122 relative to the first and second clip arms 110, 112, respectively. In one embodiment, the first and second jaws 120, 122 may pivot about the pins 134, 142, respectively, up to an angle of approximately 10 degrees relative to longitudinal axes of the first and second clip arms 110, 112, in either direction, so that the clip 102 may be moved past bends and/or curves of a body lumen through which the clip 102 is inserted. In one particular embodiment, the first and second jaws 120, 122 may pivot with respect to the first and second clip arms 110, 112, respectively, up to an angle of approximately 5 degrees in either direction.

When the first and second clip arms 110, 112 are moved out of the capsule 114 and move toward the open configuration, however, the first and second jaws 120, 122 revert to their bent configuration moving the first and second jaws 120, 122 out of engagement with the retaining structures 106 so that they rotate under the bias of the torsion spring 146 with respect to the first and second clip arms 110, 112 toward their tissue-receiving configuration. As shown in FIG. 3, in one embodiment, when the clip 102 is in the closed, insertion configuration, the teeth 148, 152 of each of the first and second jaws 120, 122, respectively, may extend along opposing sides of the clip 102 so that the first and second jaws 120, 122, when pressed together, may have a smaller profile.

Figure 8:
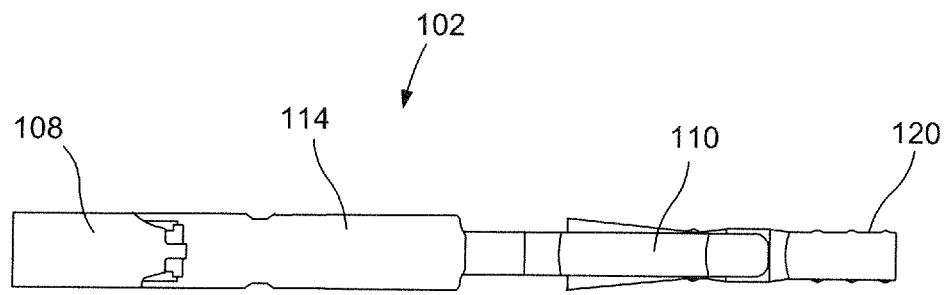
FIG. 8 shows a top plan view of the device of FIG. 1, in the closed, insertion configuration.
Figure 9:
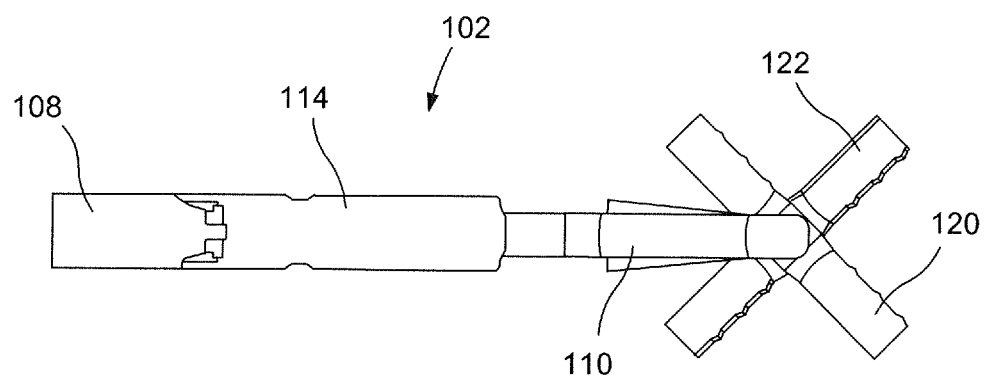
FIG. 9 shows a top plan view of the device of FIG. 1, illustrating jaws of the clip rotating relative to clip arms, when the clip arms are in the open configuration.
Figure 10:
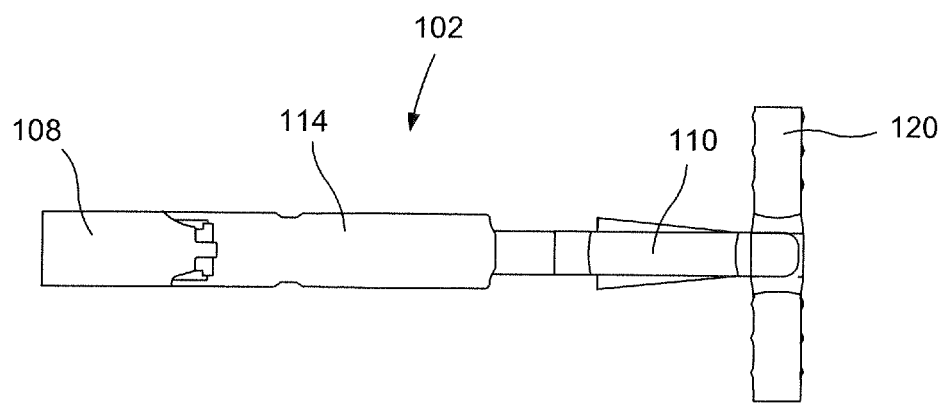
FIG. 10 shows a top plan view of the device of FIG. 1, in the open, tissue-receiving configuration.

When the clip 102 is moved toward the open, tissue-receiving configuration, the first and second jaws 120, 122 rotate, for example, in opposite directions relative to one another, as shown in FIGS. 8-10. Although the exemplary embodiment specifically show and describe torsion springs 146 facilitating rotation of the first and second jaws 120, 122 in opposite directions relative to the first and second clip arms 110, 112, it will be understood by those of skill in the art that the first and second jaws may be rotated via any of a variety of mechanisms in any of a variety of manners.

Once the clip 102 is in the open, tissue-receiving configuration, as shown in FIGS. 1, 2 and 11, the user positions the first and second jaws 120, 122 over the target tissue with the target tissue to be received between the jaws 120, 122.

As the first and second jaws 120, 122 rotate to extend transverse with respect to the first and second clip arms 110, 112, the jaws 120, 122 extend further to either side of the clip arms 110, 112 than do the ends of the clip arms and the jaws 120, 122 are dimensioned and positioned to engage tissue surrounding larger tissue defects than can be dealt with by traditional through-the scope clips, i.e., tissue openings that would previously have likely required multiple clips to close.

It will be understood by those of skill in the art that the first and second clip arms 110, 112 may be moved between the open and closed configuration (e.g., via the control wire) until the target tissue is received therebetween, as desired. Once the desired portions of target tissue are received between the first and second jaws 120, 122, the clip 102 is moved toward the closed configuration by, for example, drawing the control wire proximally relative to the capsule 114. Since drawing the control wire proximally relative to the capsule 114 moves the clip arms 110, 112 toward the closed configuration, the first and second jaws 120, 122 are also pressed against one another to grip the target tissue therebetween. In the embodiment in which the first and second jaws 120, 122 are slightly bent, pressing the first and second jaws 120, 122 against one another causes the first and second jaws 120, 122 to deform toward the straightened configuration, adding additional gripping force.

Figure 12:
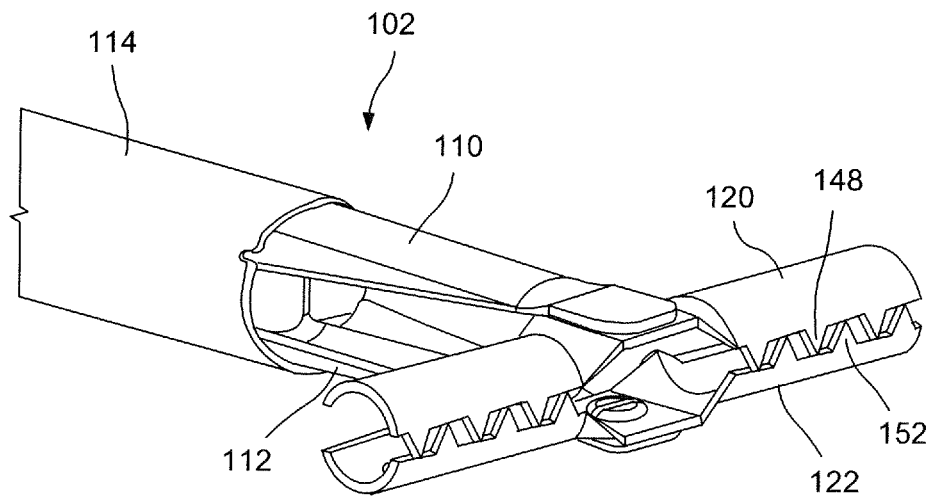
FIG. 12 shows a perspective view of the device of FIG. 1, in a closed, tissue-gripping configuration.

When the target tissue is gripped as desired, the clip 102 is locked in the closed, tissue-gripping configuration, as shown in FIG. 12. In one example, the user locks the clip 102 in the closed position by drawing the control wire proximally until locking tabs of the first and second clip arms 110, 112 engage corresponding features (e.g., windows) of the capsule 114, and release the control wire from the first and second clip arms 110, 112. As will be understood by those of skill in the art, further proximal motion of the control wire relative to the capsule 114 disengages the bushing 108 from the capsule 114 in a known manner so that the clip 102 remains deployed in the body, clipped over the target tissue.

According to an exemplary method utilizing the device 100, the clip 102 is inserted through, for example, a working channel of an endoscope to a target site within a body so that the handle member remains exterior to the body. The clip 102 is inserted through the working channel in the closed, insertion configuration, in which the first and second jaws 120, 122 are substantially aligned with the first and second clip arms 110, 112. As described above, the first and second jaws 120, 122 are permitted to pivot slightly relative to the first and second clip arms 110, 112, respectively, as the clip 102 is navigated past bends and/or curves of the working channel. Once the clip 102 is moved distally past a distal end of the working channel, to the target site, the clip 102 may be moved to the open, tissue-receiving configuration. In the open, tissue-receiving configuration, the first and second jaws 120, 122 pivot about the pins, 134, 142, respectively, so that the first and second jaws 120, 122 extend transverse to the first and second clip arms 110, 112.

Once in the tissue-receiving configuration, the clip 102 may be moved between the open and closed configurations, as desired, until the desired portion of target tissue is received between the transversely extending first and second jaws 120, 122, as desired. Upon receipt of the target tissue between the first and second jaws 120, 122, as desired, the clip 102 is moved toward the closed configuration, tissue, gripping configuration, in which the jaws 120, 122 remain transverse relative to the first and second clip arms 110, 112, as the first and second clip arms 110, 112 are moved toward one another. The clip 102 is locked and deployed in the body in the closed, tissue-gripping configuration.

It will be apparent to those skilled in the art that various modifications may be made in the present disclosure, without departing from the scope of the disclosure.

What is claimed is:

1. A clipping device, comprising:
   a proximal portion extending from a proximal end which, during use, remains outside a body accessible to a user to a distal end which, during use, is inserted into the body to a location adjacent to target tissue to be treated; and
   a clip releasably coupled to the proximal portion so that the clip may be separated from the proximal portion and left in the body clipped to target tissue when the proximal portion is withdrawn from the body, the clip comprising:
   a capsule extending longitudinally from a proximal end to a distal end and including a channel extending therethrough;
   a pair of clip arms extending from proximal ends to distal ends, the proximal ends slidably received within the channel of the capsule such that the pair of clip arms are movable relative to the capsule between an open configuration, in which the distal ends are separated from one another, and a closed configuration, in which the distal ends are moved toward one another; and
   a pair of jaws, each of the jaws pivotally coupled to a corresponding one of the clip aims and movable relative to the clip arms between an insertion configuration, in which longitudinal axes of the pair of jaws are substantially aligned with longitudinal axes of the clip arms, and a tissue-receiving configuration, in which the longitudinal axes of the pair of jaws extend transverse to the longitudinal axes of the clip aims so that a target tissue is receivable between the pair of jaws along a length thereof, the pair of jaws movable toward the tissue-receiving configuration when the pair of clip arms are in the open configuration.

2. The device of claim 1, wherein each of the jaws is coupled to the distal end of the corresponding one of the clip arms via a pin extending through a midpoint of the jaw and the distal end of the corresponding one of the clip arms.

3. The device of claim 1, wherein the pair of clip arms are biased toward the open configuration so that the pair of clip arms are constrained toward the closed configuration via an interior surface of the capsule.

4. The device of claim 1, wherein the longitudinal edges of each of the pair of clip arms include retaining structures extending toward a central plane extending between the pair of clip arms, the retaining structures maintaining a position of a corresponding one of the jaws relative to the clip aims in the insertion configuration.

5. The device of claim 4, wherein the retaining structures are configured to permit pivoting of the pair of jaws relative to the pair of clip arms up to an angle of approximately 10 degrees.

6. The device of claim 4, wherein each of the pair of jaws extends longitudinally from a first end to a second and includes a bend therealong so that the first and second ends extend toward the central plane.

7. The device of claim 4, wherein each of the pair of jaws is biased toward the tissue-receiving configuration via a torsion spring so that the pair of jaws are restrained toward the insertion configuration via the retaining structures when the clip arms are in the closed configuration.

8. The device of claim 7, wherein each of the jaws is elastically deformable toward a straightened configuration, when the pair of clip arms is in the closed configuration.

9. The device of claim 1, wherein at least one of the pair of jaws includes gripping features extending along a longitudinal edge thereof.

10. A device for treating a target tissue, comprising:
    a clip including a capsule extending longitudinally from a proximal end to a distal end and including a channel extending therethrough, proximal ends of a pair of clip arms slidably received within the channel so that the pair of clip arms are movable relative to the capsule between an open configuration, in which distal ends thereof are separated from one another, and a closed configuration, in which the distal ends thereof are moved toward one another, a pair of jaws pivotally coupled to the clip arms and movable relative to the clip arms between an insertion configuration, in which longitudinal axes of the pair of jaws are substantially aligned with longitudinal axes of the clip arms, and a tissue-receiving configuration, in which the longitudinal axes of the pair of jaws extend transverse to the longitudinal axes of the clip arms when the clip arms are in the open configuration; and
    a proximal portion configured to permit insertion of the clip through a working channel of an endoscope, the proximal portion including a bushing at a distal end thereof, the bushing releasably coupled to the proximal end of the capsule so that, upon separation of the bushing from the capsule, the clip is separated from the proximal portion to remain clipped on target tissue as the proximal portion is withdrawn from the body.

11. The device of claim 10, wherein the pair of clip arms are biased toward the open configuration so that the pair of clip arms are constrained toward the closed configuration via an interior surface of the capsule.

12. The device of claim 10, wherein the longitudinal edges of each of the pair of clip arms include retaining structures extending toward a central plane extending between the pair of clip arms, the retaining structures maintaining a position of a corresponding one of the jaws relative to the clip arms in the insertion configuration.

13. The device of claim 12, wherein each of the pair of jaws extends longitudinally from a first end to a second and includes a bend therealong so that the first and second ends extend toward the central plane.

14. The device of claim 12, wherein each of the pair of jaws is biased toward the tissue-receiving configuration via a torsion spring so that the pair of jaws are restrained toward the insertion configuration via the retaining structures when the clip arms are in the closed configuration.

15. The device of claim 10, wherein at least one of the pair of jaws includes gripping features extending along a longitudinal edge thereof.

16. A method for treating a target tissue, comprising:
    inserting a clip device, in a closed configuration, through a working channel of an endoscope to a target site within a body until the clip device extends distally past a distal end of the working channel, the clip device including a capsule and a pair of clip arms received therein and movable relative thereto between an open configuration, in which distal ends of the clip aims are separated from one another, and the closed configuration, in which the distal ends of the clip arms are drawn toward one another;

moving the clip device toward the open configuration so that a pair of jaws pivotally coupled to distal ends of the clip arms are moved from an insertion configuration, in which longitudinal axes of the pair of jaws are aligned with longitudinal axes of the clip arms, toward a tissue-receiving configuration in which the pair of jaws extend transverse relative to the clip arms, each of the pair of jaws pivotally coupled to a corresponding one of the clip arms;

positioning the pair of jaws over the target tissue so that the target tissue is received therebetween;

moving the pair of arms, with the jaws extending transverse relative thereto, toward the closed configuration to grip the target tissue between the pair of jaws; and separating the clip device from an insertion section so that the clip device may be left in the body clipped to target tissue as the insertion section is withdrawn from the body.

17. The method of claim 16, wherein the jaws pivot within retaining structures extending from longitudinal edges of each of the pair of clip arms during insertion of the clip device through the working channel to navigate past curves of the working channel.

18. The method of claim 16, wherein the pair of jaws are biased toward the tissue-receiving configuration in which the jaws extend transverse relative to the clip arms so that, when the pair of clip arms are in the open configuration, the pair of jaws revert to the biased tissue-receiving configuration.

19. The method of claim 16, wherein each of the pair of jaws extends longitudinally from a first end to a second and includes a bend therealong so that first and second ends of each of the pair of jaws extend toward a central plane extending between the pair of jaws.

20. The method of claim 19, wherein each of the pair of jaws is elastically deformable toward a straightened configuration, when the pair of clip arms are in the closed configuration.

* * * * *